United States Patent
Ramachandran et al.

(10) Patent No.: US 9,790,146 B2
(45) Date of Patent: Oct. 17, 2017

(54) PROCESS TO PRODUCE LINEAR PENTENES AND METATHESIS THEREOF

(71) Applicant: Lummus Technology Inc., Bloomfield, NJ (US)

(72) Inventors: Bala Ramachandran, Easton, PA (US); Sukwon Choi, Clifton, NJ (US)

(73) Assignee: Lummus Technology Inc., Bloomfield, NJ (US)

(*) Notice: Subject to any disclaimer, the term of this patent is extended or adjusted under 35 U.S.C. 154(b) by 0 days.

(21) Appl. No.: 15/224,951

(22) Filed: Aug. 1, 2016

(65) Prior Publication Data

US 2016/0340274 A1 Nov. 24, 2016

Related U.S. Application Data

(62) Division of application No. 14/069,737, filed on Nov. 1, 2013, now Pat. No. 9,499,458.

(60) Provisional application No. 61/728,046, filed on Nov. 19, 2012.

(51) Int. Cl.

| | | |
|---|---|---|
| *B01J 10/00* | (2006.01) | |
| *C07C 6/04* | (2006.01) | |
| *C07C 41/06* | (2006.01) | |
| *C07C 7/148* | (2006.01) | |
| *B01J 19/24* | (2006.01) | |
| *C07C 1/20* | (2006.01) | |
| *C07C 5/27* | (2006.01) | |

(52) U.S. Cl.
CPC ............. *C07C 6/04* (2013.01); *B01J 19/245* (2013.01); *C07C 1/20* (2013.01); *C07C 5/2767* (2013.01); *C07C 7/14891* (2013.01); *C07C 41/06* (2013.01); *Y02P 20/127* (2015.11)

(58) Field of Classification Search
CPC ....... C07C 41/06; C07C 6/04; C07C 7/14891; C07C 11/06; C07C 11/10; C07C 43/046; C07C 1/20; C07C 5/2767; B01J 19/245; Y02P 20/127

See application file for complete search history.

(56) References Cited

U.S. PATENT DOCUMENTS

| | | | | |
|---|---|---|---|---|
| 5,898,091 | A * | 4/1999 | Chodorge | C07C 6/04 585/271 |
| 6,143,936 | A * | 11/2000 | Marion | C07C 11/02 568/579 |
| 8,754,277 | B2 * | 6/2014 | Sadasivan Vijayakumari | C07C 1/22 549/523 |

* cited by examiner

*Primary Examiner* — Sharon Pregler
(74) *Attorney, Agent, or Firm* — Osha Liang LLP

(57) ABSTRACT

Mixed pentenes may be converted to propylene by feeding an alcohol, linear pentenes, and isopentenes to an etherification reactor. The alcohol and isopentenes may be reacted in the etherification reactor to convert isopentenes to tertiary amyl alkyl ether, which may be separated from the linear pentenes, recovered as a linear pentene fraction. The tertiary amyl alkyl ether may be fed to a decomposition reactor to convert at least a portion of the tertiary amyl alkyl ether to alcohol and isopentenes. The alcohol and isopentenes may then be separated to recover an isopentene fraction and an alcohol fraction. The isopentene fraction is then fed to a skeletal isomerization reactor to convert at least a portion of the isopentenes to linear pentenes, the effluent from which may be recycled to the etherification reactor. Ethylene and the linear pentene fraction may then be fed to a metathesis reactor to produce propylene.

23 Claims, 4 Drawing Sheets

PROCESS TO PRODUCE LINEAR PENTENES AND METATHESIS THEREOF

CROSS-REFERENCE TO RELATED APPLICATION

This application, pursuant to 35 U.S.C. §120, claims benefit to U.S. patent application Ser. No. 14/069,737 filed Nov. 1, 2013, now U.S. Pat. No. 9,499,458, which pursuant to 35 U.S.C. §119(e), claims priority to U.S. Provisional Application Ser. No. 61/728,046, filed Nov. 19, 2012. Each of these applications is incorporated herein by reference in their entirety.

FIELD OF THE DISCLOSURE

Embodiments disclosed herein relate to production of propylene via metathesis of pentenes with ethylene. More specifically, embodiments disclosed herein relate to the efficient separation and conversion of isopentenes in a mixed pentene feed (isopentenes and linear pentenes) to linear pentenes and metathesis of the linear pentenes with ethylene to form propylene.

BACKGROUND

The high demand of polypropylene is increasing. This propylene growth combined with the scarcity of butenes (for making propylene by metathesis) has created a market for the utilization of pentenes to make propylene by metathesis. C5 olefins are available from two main sources. They are (i) C5 olefins available from stream cracker, and (ii) C5 olefins available from refinery, both containing significant amounts of isopentene along with the linear pentenes.

When linear pentenes are fed to a conventional metathesis reactor, the following reactions may occur:

1-pentene-→2- pentene (Isomerization);  (a)

2-pentene+ethylene-→1-butene+propylene (Metathesis);  (b)

1-butene-→2- butene (Isomerization);  (c)

2-butene+ethylene-→2 propylene (Metathesis).  (d)

1-Pentene is isomerized to 2-pentene. The metathesis reaction of 1-pentene with ethylene is non-productive (products are same as reactants). The overall linear C5 olefin reaction can thus be shown as:

1 linear pentene+2 ethylene-→3 propylene.

When isopentenes are fed to a conventional metathesis reactor, the following reactions may occur:

2-methyl-2-butene+ethylene-→isobutene+propylene (Metathesis)

2-methyl-1-butene-→2-methyl-2- butene (Isomerization)

3-methyl-1-butene-→2-methyl-2- butene (Isomerization)

The reactions of 2-methyl-1-butene and 3-methyl-1-butene with ethylene are non-productive. Thus, the metathesis of isopentenes results in only one mole of propylene, one-third the productivity of the linear pentene metathesis.

Typically, isopentenes content in these C5 streams is in the range of 40-60 wt % and is the most abundant species. As shown in the reactions above, the processing of isopentenes by metathesis results in the inefficient conversion of pentenes to propylene. Only one mole of propylene is formed from every mole of isopentene, as opposed to three moles of propylene from every mole of linear pentene.

Table 1 shows the boiling points of the linear pentenes and the isopentenes.

TABLE 1

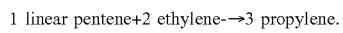

| Pentene | Boiling Point (° C.) | Type |
|---|---|---|
| 3-Methyl 1-Butene | 26.00 | Isopentene |
| 1-Pentene | 29.95 | Linear Pentene |
| 2-Methyl 1-Butene | 31.20 | Isopentene |
| t-2-Pentene | 36.30 | Linear Pentene |
| c-2-Pentene | 36.90 | Linear Pentene |
| 2-Methyl 2-Butene | 38.55 | Isopentene |

As can be seen from the staggered boiling points of the linear pentenes and the isopentenes, a simple separation of the linear pentenes from isopentenes by distillation is not easily achievable.

SUMMARY OF THE DISCLOSURE

In one aspect, embodiments disclosed herein relate to a process for converting mixed pentenes to propylene. The process may include: feeding an alcohol and a hydrocarbon stream containing linear pentenes and isopentenes to an etherification reactor, reacting the alcohol and isopentenes in the etherification reactor to convert at least a portion of the isopentenes to tertiary amyl alkyl ether, separating the linear pentenes from the tertiary amyl alkyl ether to recover a linear pentene fraction and a tertiary amyl alkyl ether fraction; feeding the tertiary amyl alkyl ether fraction to a decomposition reactor, reacting the tertiary amyl alkyl ether in the decomposition reactor to convert at least a portion of the tertiary amyl alkyl ether to alcohol and isopentenes; separating the alcohol and the isopentenes produced in the decomposition reactor to recover an isopentene fraction and an alcohol fraction; feeding the isopentene fraction to a skeletal isomerization reactor to convert at least a portion of the isopentenes to linear pentenes; recovering an effluent from the skeletal isomerization reactor comprising isopentenes and linear pentenes; recycling the effluent from the skeletal isomerization reactor to the etherification reactor and feeding ethylene and the linear pentene fraction to a metathesis reactor to convert at least a portion of the linear pentenes and ethylene to propylene.

In another aspect, embodiments disclosed herein relate to a system for converting mixed pentenes to propylene. The system may include: an etherification reactor for converting an alcohol and isopentenes to tertiary amyl alkyl ether, a separator for separating the linear pentenes from the tertiary amyl alkyl ether and to recover a linear pentene fraction and a tertiary amyl alkyl ether fraction; a decomposition reactor for reacting for converting at least a portion of the tertiary amyl alkyl ether in the tertiary amyl ether fraction to alcohol and isopentenes; a separator for separating the alcohol and the isopentenes produced in the decomposition reactor and to recover an isopentene fraction and an alcohol fraction; a skeletal isomerization reactor to convert at least a portion of the isopentenes in the isopentene fraction to linear pentenes; a flow line for recovering an effluent from the skeletal isomerization reactor comprising isopentenes and linear pentenes and recycling the effluent from the skeletal isomerization reactor to the etherification reactor, and a metathesis reactor for reacting at least a portion of the linear pentenes in the linear pentene fraction with ethylene to form propylene.

Other aspects and advantages will be apparent from the following description and the appended claims.

DETAILED DESCRIPTION

Figure 1:
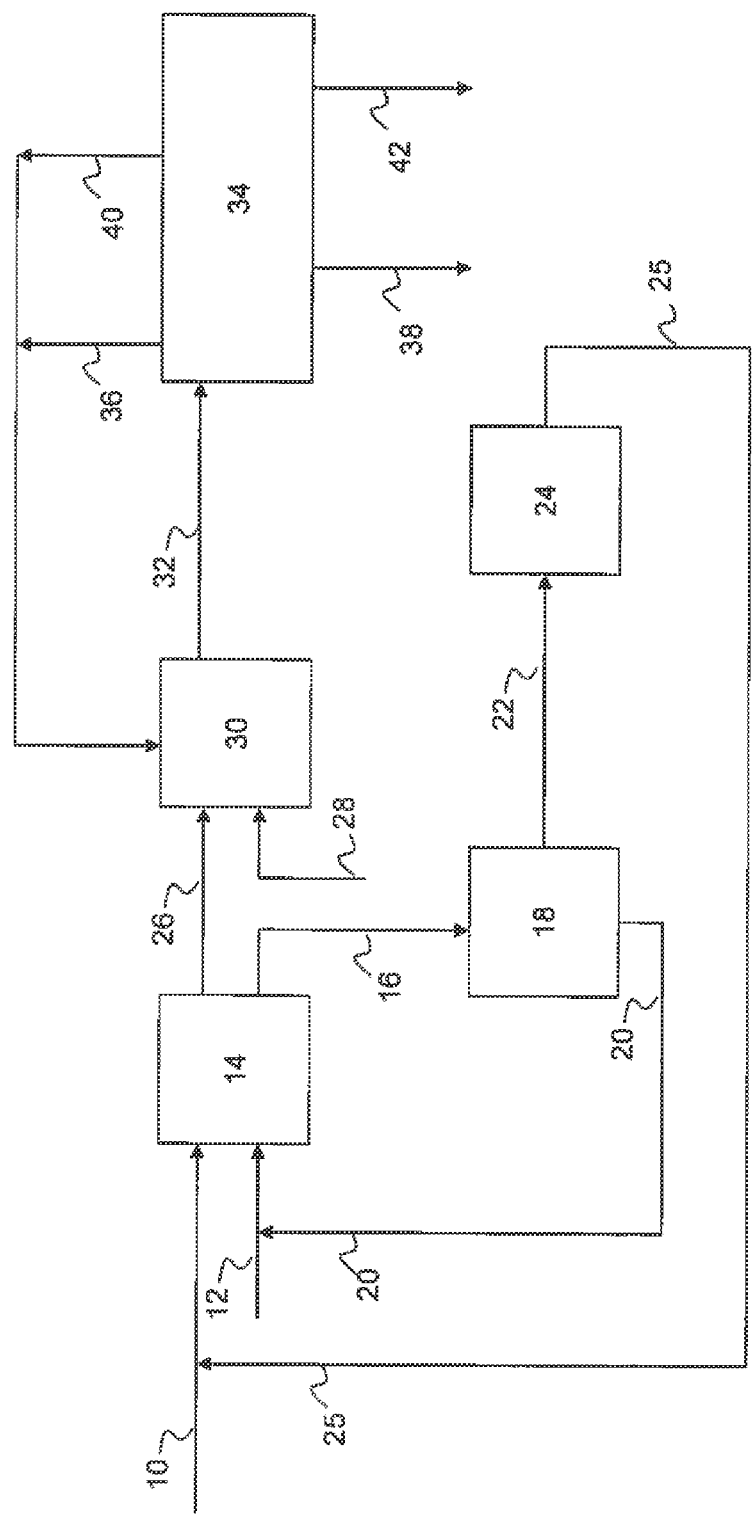
FIG. 1 is a simplified block flow diagram of a process for producing propylene from mixed pentenes according to embodiments disclosed herein.

In one aspect, embodiments disclosed herein relate to production of propylene via metathesis of pentenes with ethylene. More specifically, embodiments disclosed herein relate to the efficient separation and conversion of isopentenes in a mixed pentene feed (isopentenes and linear pentenes) to linear pentenes and metathesis of the linear pentenes with ethylene to form propylene.

To separate the isopentenes from linear pentenes, the mixed pentene feed may be fed to an etherification reactor to react at least a portion of the isopentenes with an alcohol, such as a C1 to C4 alcohol, to produce tertiary amyl alkyl ethers. Linear pentens do not react to any substantial degree in the etherification reactor. The tertiary amyl alkyl ethers, having a significantly different boiling point than the linear pentenes, may then be separated from the linear pentenes to produce a linear pentene fraction and a tertiary amyl alkyl ether fraction. The linear pentene fraction may then be fed to a metathesis reactor for conversion of the linear pentenes to propylene via metathesis with ethylene, producing up to 3 moles of propylene per mole of linear pentenes.

The tertiary amyl alkyl ether fraction may then be fed to a decomposition reactor to convert the tertiary amyl alkyl ether back into the alcohol and the isopentene. The reaction products are separated, and the alcohol may be recycled back to the etherification reactor (system may be essentially closed loop with respect to the alcohol). The decomposition reaction may be performed in one or more fixed bed reactors in the presence of a catalyst. Addition of water or a tertiary alcohol (such as tertiary amyl ether, used as a water equivalent, decomposing to an isoolefin and water) to the tertiary alkyl ether feed stream, for example, may be beneficial to suppress unwanted side reactions. Other water equivalents may additionally be used.

The isopentenes produced in the decomposition reactor may then be fed to a skeletal isomerization reactor to convert a portion of the isopentenes to linear pentenes. Skeletal isomerization is a reversible reaction, and at a temperature of about 400° C., the skeletal isomerization reactor effluent may contain about 65% to 69% isopentenes (other temperatures may result in a different equilibrium mixture). As such, a high concentration isopentene feed is beneficial, allowing for maximum shifting of the isopentenes to linear pentenes. The high concentration isopentene feed is provided by the decomposition reactor, which may provide for an essentially pure isopentene feed in some embodiments; greater than 90% isopentene in other embodiments; and greater than 80% isopentene in other embodiments.

The mixed pentenes recovered from the skeletal isomerization reactor may then be recycled back to the etherification reactor, for conversion and separation of isopentenes and forwarding of the additional linear pentenes produced via skeletal isomerization to the metathesis reactor.

Mixed pentene feedstocks useful in embodiments disclosed herein may include linear pentenes and isopentenes. Mixed pentene feedstocks may also include various other hydrocarbon components, including C4 to C6 paraffins and olefins. In some embodiments, the mixed pentene feedstock may be a C5 hydrocarbon fraction from a catalytic or steam cracker, where the C5 fraction may include linear pentenes, isopentene, n-pentanes, and isopentanes. In some embodiments, the mixed pentene feedstock may include isopentene at a concentration of greater than 40 mol %, 50 mol %, or 60 mol %.

Alcohols useful in the etherification reactor may include C1 to C4 alcohols, among others. For example, the alcohol feed to the etherification reactor may include at least one of methanol, ethanol, n-propanol, n-butanol. In some embodiments, the alcohol feed is methanol.

FIG. 1 illustrates a simplified block flow diagram of a process for producing propylene from mixed pentenes according to embodiments disclosed herein. Mixed pentenes and an alcohol, such as methanol, may be fed via flow lines 10 and 12, respectively, to etherification reaction zone 14. Etherification reaction zone 14 may include one or more etherification reactors containing an etherification catalyst. The isopentenes in the mixed pentenes may then be reacted with the alcohol at appropriate reaction conditions over the etherification catalyst to produce a reaction effluent including tertiary amyl alkyl ethers and linear pentenes. The linear pentenes and tertiary amyl alkyl ethers in the reaction effluent are then separated to form a linear pentene fraction and a tertiary amyl ether fraction.

The tertiary amyl alkyl ether fraction is fed via flow line 16 to decomposition reaction zone 18, which may include one or more reactors containing a decomposition catalyst. The tertiary amyl alkyl ether is then contacted with the decomposition catalyst at appropriate reaction conditions to crack the tertiary amyl alkyl ether into the constituent components, namely the alcohol and isopentene. The reaction products are separated into an alcohol faction, which may be recycled back to the etherification reactor via flow line 20, and an isopentene fraction.

The resulting isopentene fraction, which may be a high purity isopentene fraction (i.e., greater than 90%, 95%, 98%, or even 99% isopentene) may then be fed via flow line 22 to skeletal isomerization reaction zone 24. Skeletal isomerization reaction zone 24 may include one or more reactors containing a skeletal isomerization catalyst. The isopentene is then contacted with the skeletal isomerization catalyst at appropriate reaction conditions to convert at least a portion of the isopentene to linear pentenes. The reaction effluent from the skeletal isomerization reaction zone 24, including both linear and iso-pentenes, may then be recycled via flow line 25 to the etherification reaction zone 14, for continued reaction and separation of the isopentenes from the linear pentenes.

The linear pentene fraction recovered from etherification reaction zone 14 via flow line 26, including linear pentenes as the primary olefinic component, and ethylene feed 28 may be forwarded to metathesis reaction zone 30. Metathesis reaction zone 30 may include one or more metathesis reactors containing a metathesis catalyst. The linear pentenes and ethylene are then contacted with the metathesis catalyst at appropriate reaction conditions to convert at least a portion of the linear pentenes and ethylene to propylene.

The metathesis reaction products, including unreacted ethylene, propylene, butenes, and unreacted pentenes may then be recovered via flow line 32 and forwarded to separation zone 34. Separation zone 34 includes one or more distillation columns and/or extractive distillation columns for separating the metathesis reactor effluent into various desired fractions, which may include ethylene fraction 36, propylene fraction 38, butene/pentene fraction 40, and heavies fraction 42. If desired, ethylene fraction 36 and butene/pentene fraction 40 may be recycled to metathesis reaction zone 30 for continued production of propylene.

Catalysts useful in the etherification reactor may include any catalyst typically used in etherification processes, such as conventional cation exchange resins and/or zeolites. Examples of etherification catalysts useful in embodiments disclosed herein are described in, for example, U.S. Pat. No. 7,553,995, which is incorporated herein by reference. Other suitable etherification catalysts are described in, for example, U.S. Pat. Nos. 5,190,730, 5,231,234, 5,248,836, 5,292,964, 5,637,777, and 6,107,526, among others.

Operating conditions in the etherification reactor may vary based on the feed mixture, reactor type, reactor/reaction phase(s), catalyst type, and other variables known to those skilled in the art. Etherification reaction conditions may include, for example, a temperature in the range from about 30° C. to about 150° C. in some embodiments; from 50° C. to 120° C. in other embodiments; and from 80° C. to 110° C. in yet other embodiments, where the pressure may range from 0.5 bar to 10 bar in some embodiments, and from 1 bar to 5 bar in other embodiments.

Catalysts useful in the decomposition reactor may include any decomposition catalyst, which may include various supported and unsupported acid catalysts. Acid catalysts that may be used according to embodiments herein may include solid acid catalysts, natural clays, synthetic clays, zeolites or molecular sieves, acid resin catalysts, such as solfonic acid resins or acid cation exchange resins, and others as known to those skilled in the art. In some embodiments, the decomposition catalyst may include an HF treated amorphous synthetic alumina-silica catalyst or a selectively poisoned HF treated amorphous synthetic alumina-silica catalyst, such as disclosed in U.S. patent application Ser. No. 12/260,729, which is incorporated herein by reference.

Operating conditions in the decomposition reactor may vary based on the feed mixture, reactor type, catalyst type, reactor/reaction phase(s), and other variables known to those skilled in the art. Decomposition temperatures may range from 100° C. to 500° C. in some embodiments; from 130 to 350° C. in other embodiments and from 150° C. to 300° C. in yet other embodiments. The decomposition reaction may be carried out under pressures in the range from 1 to 22 bar (0 to 300 psig) in some embodiments; from 1 to 11 bar (0 to 150 psig) in other embodiments. In some embodiments, the pressure is maintained such that the product olefin is in the liquid phase or partially in the liquid phase at the reaction temperature used. The liquid hourly space velocity (LHSV) (the volume of liquid per volume of catalyst per hour) at which the reaction is carried out may be within the range from 0.5 to 200 $h^{-1}$ in some embodiments; from 1 to 50 $h^{-1}$ in other embodiments; and from 1 to 10 $h^{-1}$ in yet other embodiments.

Catalysts useful in the skeletal isomerization reactor may include promoted acidic catalysts. In some embodiments, the skeletal isomerization catalyst may include a molecular sieve or zeolite catalyst, such as a silica/alumina phosphate (SAPO), ZSM-22, ZSM-23, or various molecular sieves having a 10-membered ring structure, such as disclosed in EP0703888B1. Various metallosilicate skeletal isomerization catalysts are disclosed in, for example, U.S. Pat. No. 5,019,661. Other catalysts that may be used for skeletal isomerization disclosed herein include those disclosed in, for example, U.S. Pat. No. 4,650,917.

Operating conditions in the skeletal isomerization reactor may vary based on the feed mixture, reactor type, catalyst type, reactor/reaction phase(s), and other variables known to those skilled in the art. Skeletal isomerization reaction temperatures may range from 50° C. to 500° C. in some embodiments; from 125 to 400° C. in other embodiments and from 150° C. to 350° C. in yet other embodiments. The skeletal isomerization reaction may be carried out under pressures in the range from 1 to 50 bar in some embodiments; from 2 to 40 bar in other embodiments. The olefin-containing feed may be supplied to the catalyst at a weight hourly space velocity (WHSV) in the range from about 0.1 to about 100 $h^{-1}$, and with a hydrogen partial pressure, when used, in the range from about 0.1 to 30 bar. As competing hydrogenation reactions may occur, depending upon hydrogen partial pressures and temperatures used, as well as the fact that the skeletal isomerization reaction is reversible, typically achieving equilibrium in the reactor, where the equilibrium point may be temperature dependent, care should be taken when selecting the appropriate reaction conditions.

Catalysts useful in the metathesis reactor may include any known metathesis catalyst, including oxides of Group VIA and Group VIIA metals on supports. Catalyst supports can be of any type and could include alumina, silica, mixtures thereof, zirconia, and zeolites. In addition to the metathesis catalyst, the catalyst contained in the metathesis reactor may include a double bond isomerization catalyst such as magnesium oxide or calcium oxide, for converting 1-butene and 1-pentene to 2-butene and 2-pentene, allowing for increased production of propylene via metathesis with ethylene. In some embodiments, the catalyst may include a promoter to reduce acidity; for example, an alkali metal (sodium, potassium or lithium), cesium, a rare earth, etc. In some embodiments, the metathesis or mixed metathesis/double bond isomerization catalyst may include those described in US20110021858 or US20100056839, for example.

The metathesis reactor may operate at a pressure between 1 and 40 bar in some embodiments, and between 5 and 15 bar in other embodiments. The metathesis reactor may be operated such that the reaction temperature is within the range from about 50° C. to about 600° C.; within the range from about 200° C. to about 450° C. in other embodiments; and from about 250° C. to about 400° C. in yet other embodiments. The metathesis reaction may be performed at a weight hourly space velocity (WHSV) in the range from about 3 to about 200 in some embodiments, and from about 6 to about 40 in other embodiments. The reaction may be carried out in the liquid phase or the gas phase, depending on structure and molecular weight of the olefin(s), by contacting the olefin(s) with the metathesis catalyst. If the reaction is carried out in the liquid phase, solvents or diluents for the reaction can be used, such as aliphatic saturated hydrocarbons, e.g., pentanes, hexanes, cyclohexanes, dodecanes, and aromatic hydrocarbons such as benzene and toluene are suitable. If the reaction is carried out in the gaseous phase, diluents such as saturated aliphatic hydrocarbons, for example, methane, ethane, and/or substantially inert gases, such as nitrogen and argon, may be present. For high product yield, the reaction may be conducted in the absence of significant amounts of deactivating materials such as water and oxygen.

Figure 2:
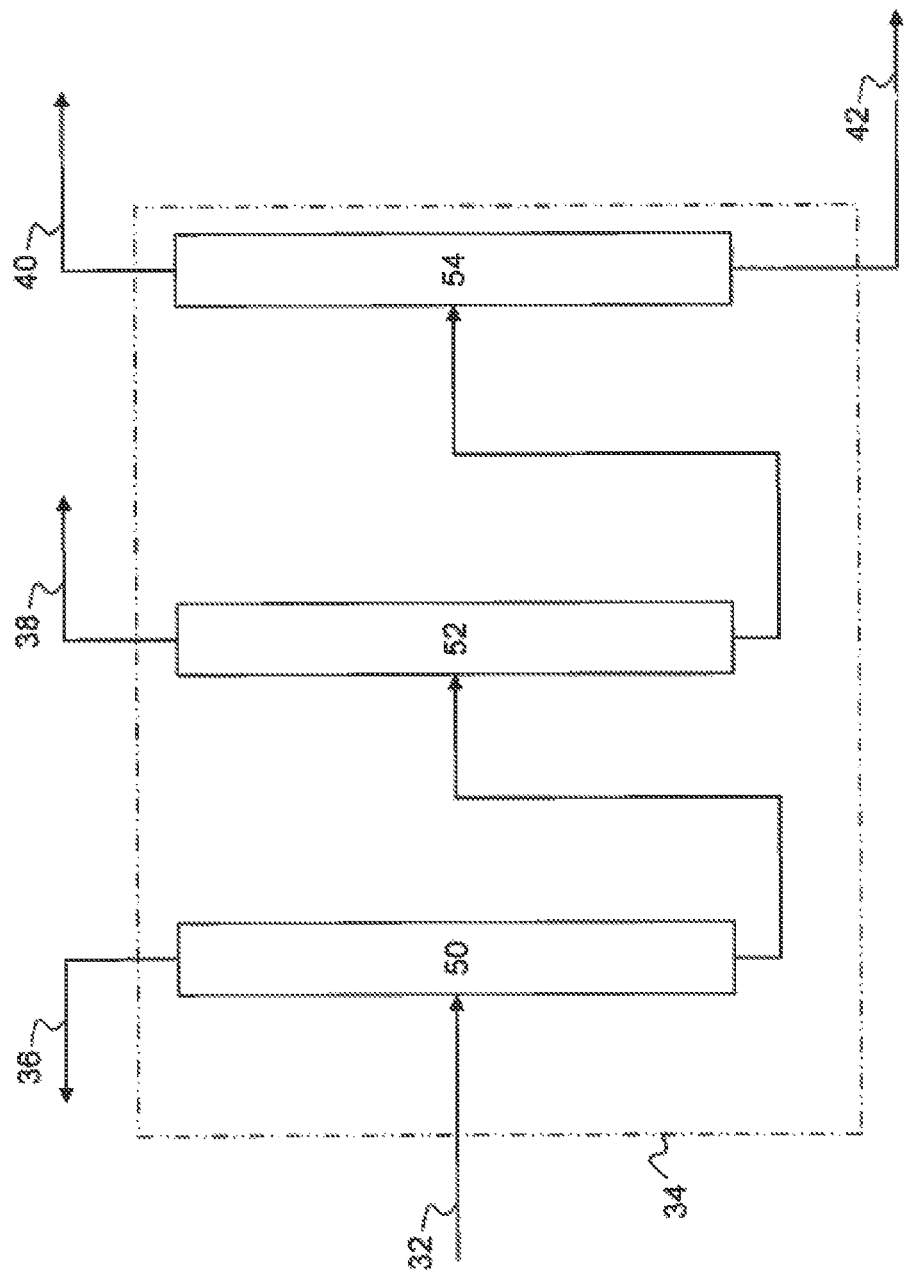
FIG. 2 is a simplified process flow diagram of a separation scheme useful in embodiments disclosed herein.

Separation of the products from the metathesis reactor may be performed using any number of combinations of distillation and/or extractive distillation columns. In some embodiments, such as illustrated in FIG. 2, the metathesis reactor effluent may be fed to a series of distillation columns including a deethanizer 50, a depropanizer 52, and a depentenizer 56 for separation and recovery of the ethylene recycle fraction 36, the propylene product fraction 38, the C4/C5 recycle fraction 40, and the C5+ purge fraction 42. Other various separation schemes may also be used, and as may be readily envisioned by one skilled in the art, for separating C2, C3, C4, C5, and heavier hydrocarbon components.

The etherification unit and the decomposition unit may include fixed bed reactor(s), moving bed reactor(s) or other types of reactors. Examples of various reactors useful in embodiments disclosed herein may include tubular reactors, boiling point reactors, bubble column reactors, traditional fixed bed reactors, catalytic distillation column reactor systems, pulsed flow reactors, and combinations thereof. One or more of such reactors may be used in parallel flow or series flow, and each reactor may include one or more reaction zones containing one or more suitable decomposition catalysts.

Figure 3:
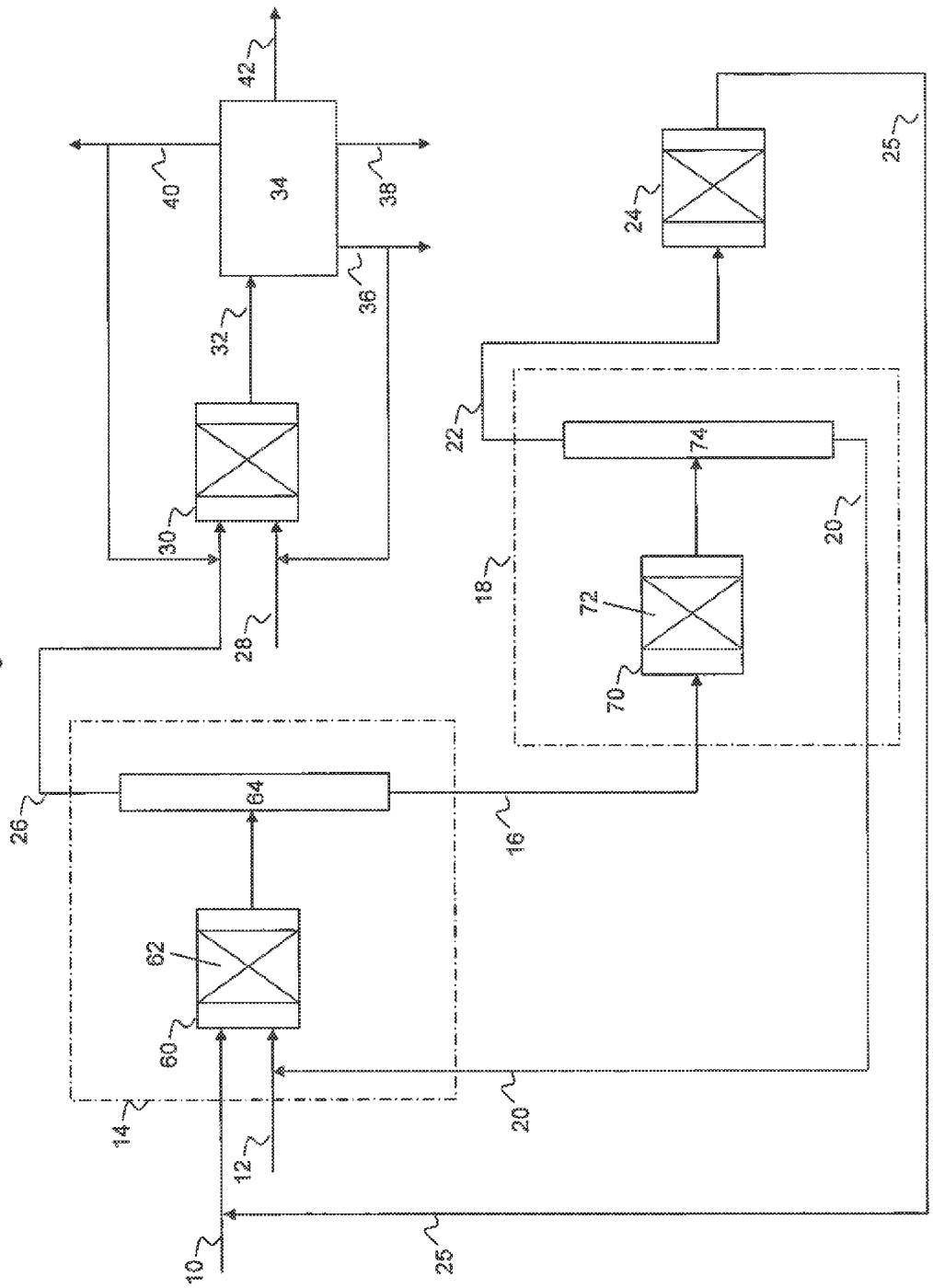
FIG. 3 is a simplified process flow diagram of a process for producing propylene from mixed pentenes according to embodiments disclosed herein.

In some embodiments, the etherification unit and/or the decomposition unit may include fixed bed reactor(s) that are followed by a separator, such as a distillation column, for separating the reactor effluent into various desired fractions, as illustrated in FIG. 3, where like numerals represent like parts. As illustrated, etherification reaction zone 14 may include an etherification reactor 60 containing etherification catalyst bed 62, the effluent from which may be fed to separator 64 for separation of tertiary amyl ether fraction 16 from linear pentene fraction 26. Likewise, decomposition reaction zone 18 may include a decomposition reactor 70 containing decomposition catalyst bed 72, the effluent from which may be fed to separator 74 for separation of alcohol fraction 20 from isopentene fraction 22.

Figure 4:
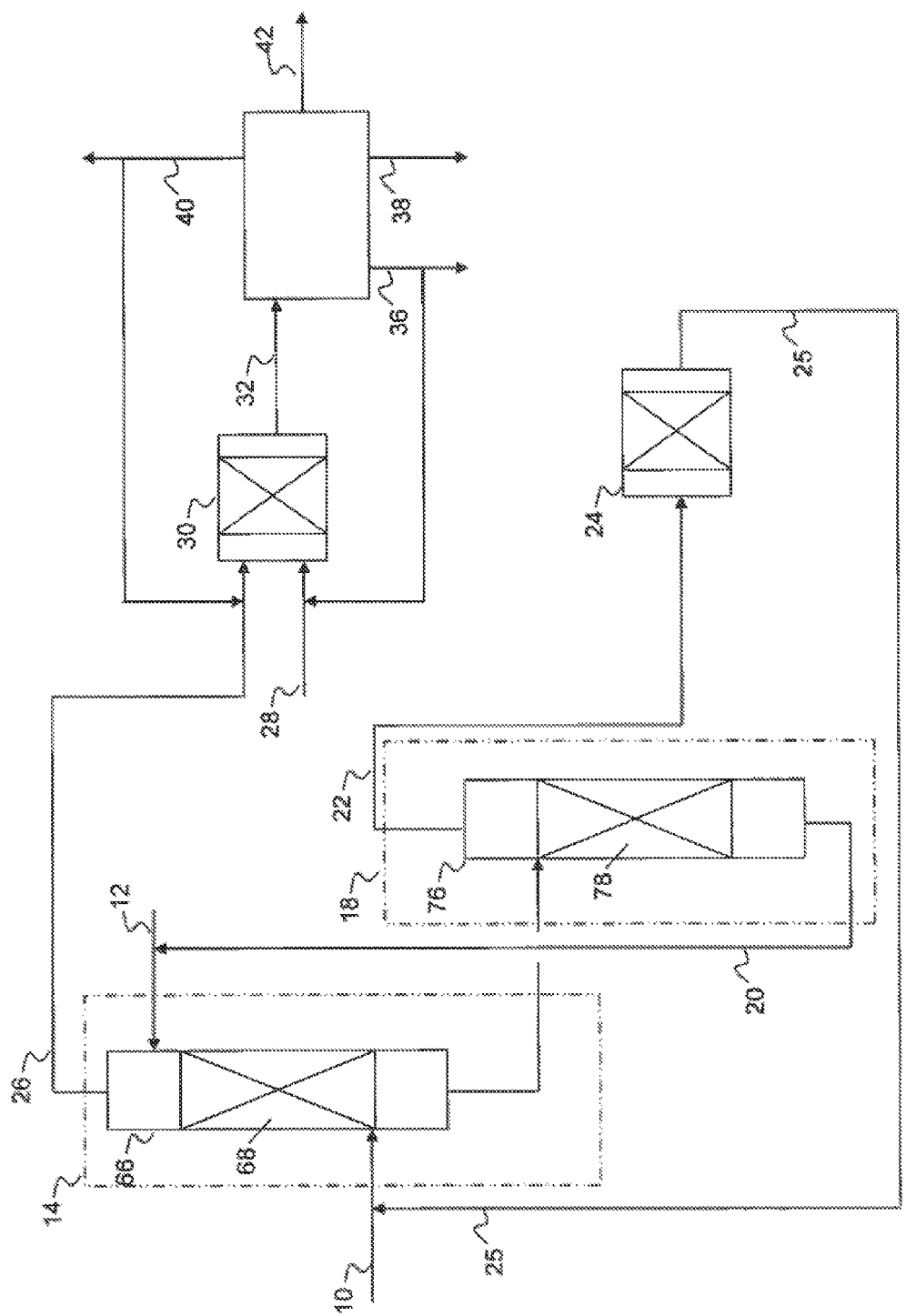
FIG. 4 is a simplified process flow diagram of a process for producing propylene from mixed pentenes according to embodiments disclosed herein.

In other embodiments, the etherification unit and/or the decomposition unit may combine the reacting and separating steps in a catalytic distillation reactor system, as illustrated in FIG. 4, where like numerals represent like parts. As illustrated, etherification reaction zone 14 may include a catalytic distillation etherification reaction system 66 containing etherification catalyst bed 68, for concurrently (i) reacting the alcohol and isopentene to form tertiary amyl alkyl ethers, (ii) separating the tertiary amyl alkyl ethers from the linear pentenes, (iii) recovering the linear pentene fraction 26 as an overheads fraction, and (iv) recovering the tertiary amyl alkyl ether fraction 16 as a bottoms fraction. Likewise, decomposition reaction zone 18 may include a catalytic distillation decomposition reaction system 76 containing decomposition catalyst bed 78, for concurrently (i) cracking the tertiary amyl alkyl ether to form isopentene and alcohol, (ii) separating the alcohol from the isopentene, (iii) recovering the isopentene fraction 22 as an overheads fraction, and (iv) recovering the alcohol fraction 20 as a bottoms fraction.

Within the scope of this application, the expression "catalytic distillation reactor system" denotes an apparatus in which the catalytic reaction and the separation of the products take place at least partially simultaneously. The apparatus may comprise a conventional catalytic distillation column reactor, where the reaction and distillation are concurrently taking place at boiling point conditions, or a distillation column combined with at least one side reactor, where the side reactor may be operated as a liquid phase reactor or a boiling point reactor. Divided wall distillation columns, where at least one section of the divided wall column contains a catalytic distillation structure, may also be used, and are considered "catalytic distillation reactor systems" herein.

Various combinations of fixed bed reactors upstream (pre-reactor) and downstream (finishing reactor) of the catalytic distillation reactor systems are also contemplated for producing propylene according to embodiments disclosed herein.

While separators useful in embodiments disclosed herein are described above with respect distillation columns and extractive distillation columns, liquid-liquid separations, extractions, or other separation processes known to those of skill in the art may also be used. Further, where a single reactor is illustrated, such as for the skeletal isomerization reaction zone, the metathesis reaction zone, the etherification reaction zone, and/or the decomposition reaction zone, embodiments herein also contemplate use of multiple reactors in series, parallel, or a combination thereof.

As described above, embodiments disclosed herein may provide an efficient process for converting mixed pentenes to propylene. The mixed pentenes (linear and isopentenes) are processed through a TAME (tertiary amyl methyl ether) unit. The isopentenes are reacted with methanol to produce TAME. However, the linear pentenes remain unconverted in this unit. The unconverted linear pentenes stream from the TAME unit is an ideal feed for metathesis, and is sent to a metathesis reactor to produce propylene. High purity TAME that is produced from the TAME unit is then cleaved in a TAME decomposition unit, to produce back the isopentenes and methanol. The high purity isopentenes (without linear pentenes) are then processed through a skeletal isomerization unit to convert the isopentenes to linear pentenes. The effluent from the skeletal isomerization unit, containing a mixture of linear pentenes and unconverted isopentenes, is then sent to the TAME unit. Methanol recovered during the decomposition of TAME is recycled back to the TAME unit. By using TAME or other tertiary amyl alkyl ethers as an intermediate, the separation of isopentenes from the linear pentenes is successfully accomplished, and the preferred linear pentenes are selectively produced in the skeletal isomerization step. This allows for the efficient conversion of pentenes to propylene (i.e., linear pentenes to propylene), where the overall scheme allows the use of linear pentenes (with ethylene) to produce propylene without any substantial loss of carbons to undesired side products. Due to the conversion of isopentenes to linear pentenes, processes disclosed herein may allow for production of 36% to 67% higher amounts of propylene as compared to metathesis of mixed pentenes.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A system for converting mixed pentenes, including linear pentenes and isopentenes, to propylene, the system comprising
   an etherification reactor for converting an alcohol and isopentenes to tertiary amyl alkyl ether;

a separator for separating the linear pentenes from the tertiary amyl alkyl ether and to recover a linear pentene fraction and a tertiary amyl alkyl ether fraction;

a decomposition reactor for converting at least a portion of the tertiary amyl alkyl ether in the tertiary amyl ether fraction to the alcohol and isopentenes;

a separator for separating the alcohol and the isopentenes produced in the decomposition reactor and to recover an isopentene fraction and an alcohol fraction;

a skeletal isomerization reactor to convert at least a portion of the isopentenes in the isopentene fraction to linear pentenes;

a flow line for recovering an effluent from the skeletal isomerization reactor comprising isopentenes and linear pentenes and recycling the effluent from the skeletal isomerization reactor to the etherification reactor;

a metathesis reactor for reacting at least a portion of the linear pentenes in the linear pentene fraction with ethylene to form propylene.

2. The system of claim 1, further comprising a flow line for recycling at least a portion of the alcohol fraction to the etherification reactor.

3. The system of claim 1, further comprising:
a flow line for recovering an effluent from the metathesis reactor comprising ethylene, propylene, C4 olefins, C5 olefins, and heavier hydrocarbon byproducts; and,
a separator for separating the effluent from the metathesis reactor to recover an ethylene fraction, a propylene fraction, a mixed C4/C5 fraction, and a heavies purge fraction.

4. The system of claim 3, further comprising a flow line for recycling the ethylene fraction to the metathesis reactor.

5. The system of claim 3, further comprising a flow line for recycling the mixed C4/C5 fraction to the metathesis reactor.

6. The system of claim 1, wherein the etherification reactor and the separator for separating the linear pentenes are integral, as a catalytic distillation reactor system for concurrently reacting the alcohol and isopentenes and separating the linear pentenes from the tertiary amyl alkyl ether.

7. The system of claim 1, wherein the decomposition reactor and the separator for separating the alcohol and the isopentenes are integral, as a catalytic distillation reactor system for reacting the tertiary amyl alkyl ether and separating the alcohol and the isopentenes produced.

8. A system for converting mixed pentenes to propylene, comprising:
an etherification reactor for receiving an alcohol and a hydrocarbon stream containing linear pentenes and isopentenes and for converting at least a portion of the isopentenes to tertiary amyl alkyl ether;
a decomposition reactor for converting at least a portion of the tertiary amyl alkyl ether to the alcohol and isopentenes;
a skeletal isomerization reactor to convert at least a portion of the isopentenes recovered from the decomposition reactor to linear pentenes; and
a metathesis reactor for reacting at least a portion of the linear pentenes in the linear pentene fraction with ethylene to form propylene.

9. The system of claim 8, further comprising a separator for receiving an effluent from the etherification reactor and for separating the linear pentenes from the tertiary amyl alkyl ether to recover a linear pentene fraction and a tertiary amyl alkyl ether fraction.

10. The system of claim 8, wherein the etherification reactor is a catalytic distillation reactor system for concurrently:
converting at least a portion of the isopentenes to tertiary amyl alkyl ether; and
separating the linear pentenes from the tertiary amyl alkyl ether to recover a linear pentene fraction and a tertiary amyl alkyl ether fraction.

11. The system of claim 8, further comprising a separator for separating the alcohol and the isopentenes produced in the decomposition reactor to recover an isopentene fraction and an alcohol fraction.

12. The system of claim 8, wherein the decomposition reactor is a catalytic distillation reactor system for concurrently:
converting at least a portion of the tertiary amyl alkyl ether to alcohol and isopentenes; and
separating the alcohol and the isopentenes produced in the decomposition reactor and to recover an isopentene fraction and an alcohol fraction.

13. The system of claim 8, further comprising a flow line for recycling an effluent from the skeletal isomerization reactor comprising isopentenes and linear pentenes to the etherification reactor.

14. The system of claim 8, further comprising a flow line for recycling at least a portion of the alcohol fraction to the etherification reactor.

15. The system of claim 8, further comprising:
a flow line for recovering an effluent from the metathesis reactor comprising ethylene, propylene, C4 olefins, C5 olefins, and heavier hydrocarbon byproducts; and,
a separator for separating the effluent from the metathesis reactor to recover an ethylene fraction, a propylene fraction, a mixed C4/C5 fraction, and a heavies purge fraction.

16. The system of claim 15, further comprising a flow line for recycling the ethylene fraction to the metathesis reactor.

17. The system of claim 15, further comprising a flow line for recycling the mixed C4/C5 fraction to the metathesis reactor.

18. A system for converting mixed pentenes to propylene, comprising:
a catalytic etherification reactor for receiving an alcohol and a hydrocarbon stream containing linear pentenes and isopentenes and concurrently:
converting at least a portion of the isopentenes to tertiary amyl alkyl ether; and
separating the linear pentenes from the tertiary amyl alkyl ether to recover a linear pentene fraction and a tertiary amyl alkyl ether fraction
a catalytic distillation decomposition reactor for receiving the tertiary amyl alkyl ether fraction and concurrently:
converting at least a portion of the tertiary amyl alkyl ether to the alcohol and isopentenes; and
separating the alcohol and the isopentenes produced and to recover an isopentene fraction and an alcohol fraction;
a skeletal isomerization reactor to convert at least a portion of the isopentenes recovered from the decomposition reactor to linear pentenes; and
a metathesis reactor for reacting at least a portion of the linear pentenes in the linear pentene fraction with ethylene to form propylene.

19. The system of claim 18, further comprising a flow line for recycling an effluent from the skeletal isomerization reactor comprising isopentenes and linear pentenes to the etherification reactor.

20. The system of claim 18, further comprising a flow line for recycling at least a portion of the alcohol fraction to the etherification reactor.

21. The system of claim 18, further comprising:
 a flow line for recovering an effluent from the metathesis reactor comprising ethylene, propylene, C4 olefins, C5 olefins, and heavier hydrocarbon byproducts; and,
 a separator for separating the effluent from the metathesis reactor to recover an ethylene fraction, a propylene fraction, a mixed C4/C5 fraction, and a heavies purge fraction.

22. The system of claim 21, further comprising a flow line for recycling the ethylene fraction to the metathesis reactor.

23. The system of claim 21, further comprising a flow line for recycling the mixed C4/C5 fraction to the metathesis reactor.

* * * * *